(12) United States Patent
Nagasawa et al.

(10) Patent No.: US 6,884,810 B2
(45) Date of Patent: Apr. 26, 2005

(54) BENZIMIDAZOLE DERIVATIVES

(75) Inventors: Masaaki Nagasawa, Saitama (JP); Hiroyasu Nishioka, Saitama (JP); Kazuyasu Asami, Saitama (JP); Naoyoshi Miura, Saitama (JP); Yutaka Shinozaki, Saitama (JP); Hitoshi Morita, Saitama (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/380,158

(22) PCT Filed: Sep. 18, 2002

(86) PCT No.: PCT/JP02/09551

§ 371 (c)(1),
(2), (4) Date: Mar. 17, 2003

(87) PCT Pub. No.: WO03/024957

PCT Pub. Date: Mar. 27, 2003

(65) Prior Publication Data

US 2003/0236411 A1 Dec. 25, 2003

(30) Foreign Application Priority Data

Sep. 18, 2001 (JP) .......................................... 2001-282918
Mar. 29, 2002 (JP) .......................................... 2002-96101

(51) Int. Cl.[7] .......................................... A61K 31/4439
(52) U.S. Cl. .................................... 514/338; 546/273.7
(58) Field of Search ................................ 514/338, 388; 546/273.7

(56) References Cited

U.S. PATENT DOCUMENTS

| 4,255,431 | A |   | 3/1981  | Junggren et al. |         |
|-----------|---|---|---------|-----------------|---------|
| 4,508,905 | A |   | 4/1985  | Junggren et al. |         |
| 4,628,098 | A | * | 12/1986 | Nohara et al.   | 546/273.7 |
| 4,689,333 | A |   | 8/1987  | Nohara et al.   |         |
| 4,738,975 | A |   | 4/1988  | Nohara et al.   |         |
| 4,758,579 | A |   | 7/1988  | Kohl et al.     |         |
| 5,013,743 | A | * | 5/1991  | Iwahi et al.    | 514/338 |
| 5,045,552 | A |   | 9/1991  | Souda et al.    |         |
| 5,223,515 | A | * | 6/1993  | Mikura et al.   | 514/322 |
| 5,840,910 | A |   | 11/1998 | Souda et al.    |         |
| 5,877,192 | A |   | 3/1999  | Lindberg et al. |         |
| 5,998,445 | A |   | 12/1999 | Souda et al.    |         |

FOREIGN PATENT DOCUMENTS

| EP | 0 208 452   | 1/1987  |
| EP | 268956      | 6/1988  |
| EP | 356143      | 2/1990  |
| EP | 382489      | 8/1990  |
| JP | 54-141783   | 11/1979 |
| JP | 61-022079   | 1/1986  |
| JP | 61-050978   | 3/1986  |
| JP | 62-205077   | 9/1987  |
| JP | 64-006270   | 1/1989  |
| WO | WO 94/27988 | 12/1994 |

OTHER PUBLICATIONS

T. Ando, et al., Proceedings of the Japanese Society of Gastric Secretion Research, vol. 34, pp. 39–40, "Study on the Treatment of Gastric Ulcer Considering the Characteristics of Genetic Polymorphism of the Metabolic Enzyme CYP2C19", Aug. 31, 2002 (with English translation).

T. Shimatani, et al., Proceedings of the Japanese Society of Gastric Secretion Research, vol. 34, pp. 99–103, "Are Proton Pump Inhibitors the Most Potent Gastric Acid Secretion Inhibitors?", Aug. 31, 2002, (with English translation).

J. Kodaira, et al., Proceedings of the Japanese Society of Gastric Secretion Research, vol. 34, pp. 105–108, "Relation Between Acid Secretion Inhibition Effect of PPIS and CYP2C19 Genetic Polymorphisms in H. Pylori–Negative Healthy Volunteers", Aug. 31, 2002 (with English translation).

H. Saito, et al., Proceedings of the Japanese Society of Gastric Secretion Research, vol. 34, pp. 109–112, "Acid Secretion Inhibition Effect of PPI at an Initial Stage of Administration (in the Case of CYP2C19EM)", Aug. 31, 2002 (with English translation).

T. Ishizaki, Nikkei Medical, PP12001 No. 7, pp. 174–175, "What do the Latest Findings in Clinical Pharmacology Say About Choosing the Right PPI?", Feb. 2001 (with English translation).

(Continued)

Primary Examiner—Patricia L. Morris
(74) Attorney, Agent, or Firm—Oblon, Spivak, McClelland, Maier & Neustadt, P.C.

(57) ABSTRACT

A benzimidazole derivative of formula (1):

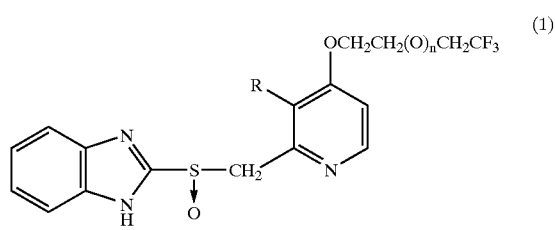

(wherein R represents a hydrogen atom or a methoxy group, and n is 0 or 1) or a salt thereof; and a medicament containing the same.

The compounds of the present invention, due to minimized difference in therapeutic effect between subjects, which difference would otherwise be derived from different CYP2C19 activity from subject to subject, ensure that all patients can enjoy proper therapeutic effects at the same dose of the drug. Also, the compounds of the invention have low risk of drug interaction caused by induction of CYP1A family member enzymes, as well as low risk of development of cancer, and thus is useful as a remedy for peptic ulcer, reliably providing therapeutic effects with safety.

11 Claims, No Drawings

OTHER PUBLICATIONS

K. Adachi, et al., Aliment Pharmacol Ther, vol. 14, pp. 1259–1266, "CYP2C19 Genotype Status and Intragastric pH During Dosing with Lansoprazole or Rabeprazole", 2000.

T. Andersson, Clin. Pharmacokinet., vol. 31, No. 1, pp. 9–28, "Pharmacokinetics, Metabolism and Interactions of Acid Pump Inhibitors", Jul. 1996.

Y. Horai, et al., Aliment Pharmacol Ther, vol. 15, pp. 793–803, "Pharmacodynamic Effects and Kinetic Disposition of Rabeprazole in Relation to CYP2C19 Genotypes", 2001.

S. Krusekopf, et al., Xenobiotica, vol. 27, No. 1, pp. 1–9, "Effects of Benzimidazole Derivatives on Cytochrome P450 1A1 Expression in a Human Hepatoma Cell Line", 1997.

T. Furuta, et al., Annals of Internal Medicine, vol. 129, No. 12, pp. 1027–1030, "Effect of Genetic Differences in Omeprazole Metabolism on Cure Rates for *Helicobacter Pylori* Infection and Peptic Ulcer", Dec. 15, 1998.

T. Furuta, et al., Gastroenterology, vol. 120, Supp. 1, #2203, p. A432, "Effects of Genotypic Differences in CYP2C19 Status on the Cure Rates for Gastoesophageal Reflux Disease by Lansoplazole", 2001.

S.– H. Park, et al., Gastroenterology, vol. 120, Supp. 1, #2219, p. A435, "Effect of CYP2C19 Polymorphism on Rabeprazole Induced Nocturnal Acid Breakthrough", 2001.

M. Sagar, et al., Aliment Pharmacol Ther, vol. 13, pp. 453–456, "Effect of CYP2C19 Polymorphism on Serum Levels of Vitamin $B_{12}$ in Patients on Long–Term Omeprazole Treatment", 1999.

T. Kokufu, et al., Eur J Clin Pharmacol, vol. 48, pp. 391–395, "Effects of Lansoprazole on Pharmacokinetics and Metabolism of Theophylline", 1995.

D. Diaz, et al., Gastroenterology, vol. 99, No. 3, pp. 737–747, "Omeprazole is an Aryl Hydrocarbon–Like Inducer of Human Hepatic Cytochrome P450", Sep. 1990.

Proceedings of the Japanese Society of Gastric Secretion Research, vol. 34, pp. 39–40, 2002.

Proceedings of the Japanese Society of Gastric Secretion Research, vol. 34, pp. 99–103, 2002.

Proceedings of the Japanese Society of Gastric Secretion Research, vol. 34, pp. 105–108, 2002.

Proceedings of the Japanese Society of Gastric Secretion Research, vol. 34, pp. 109–112, 2002.

Nlkkei Medical, pp. 174–175, Feb. 2001.

K. Adachi, et al., Aliment Pharmacol Ther, vol. 14, pp. 1259–1266, "CYP2C19 Genotype Status and Intragastric PH During Dosing with Lansoprazole or Rabeprazole", 2000.

* cited by examiner

BENZIMIDAZOLE DERIVATIVES

TECHNICAL FIELD

The present invention relates to a benzimidazole derivative that do not differ in therapeutic effect between subjects. The benzimidazole derivatives of the present invention are very safe and thus are useful as remedies for for peptic ulcers.

BACKGROUND ART

Proton pump ($H^+/K^+$-ATPase) inhibitors powerfully inhibit secretion of gastric acid, which is the major cause of peptic ulcers. Therefore, the inhibitors are widely used as remedies for peptic ulcers. Examples of proton pump inhibitors heretofore known (hereinafter referred to as "existing proton pump inhibitors") include omeprazole, esomeprazole, lansoprazole, rabeprazole, and pantoprazole (Japanese Patent Application Laid-Open (kokai) No. 54-141783, WO94/27988, Japanese Patent Application Laid-Open (kokai) No. 61-50978, Japanese Patent Application Laid-Open (kokai) No. 64-6270, and Japanese Patent Application Laid-Open. (kokai) No. 61-22079).

In recent years, analyses of pharmacokinetics have revealed that existing proton pump inhibitors are primarily metabolized by CYP2C19, which is an isoform of cytochrome P450 (CYP) (Clin. Pharmacokinet., 1996, Vol. 31, p 9–28; U.S. Pat. No. 5,877,192; Aliment. Pharmacol. Ther., 2001, Vol. 15, p 793–803). Also, many of the existing proton pump inhibitors have been known to induce CYP1A2, another isoform of cytochrome P450 (Xenobiotica, 1997, Vol. 27, No. 1, p 1–9).

Genetic polymorphism of CYP2C19 has been identified in humans, and accordingly, some humans are poor metabolizers which were hereditarily deficient in CYP2C19 activity, whereas others are extensive metabolizers exhibiting CYP2C19 activity. Thus, it has been accepted that, when existing proton pump inhibitors—which are metabolized by CYP2C19—are administered to extensive metabolizers in usual doses, in some cases, the efficacy of the inhibitors they produce in response is inferior to that produced by poor metabolizers (Ann. Intern. Med., 1998, Vol. 129, 1027–1030; Gastroenterology, 2001, Vol. 120, Suppl. 1., A-432, (#2203); and Gastroenterology, 2001, Vol. 120, Suppl. 1., A-435, (#2219)). Therefore, one approach toward causing extensive metabolizers to respond to these drugs as effectively as do poor metabolizers is to administer the drugs at higher doses to extensive metabolizers. However, administration at such a high dose is not necessary for poor metabolizers, and raises the incidence of side effects.

For the above-described reasons, when an existing proton pump inhibitor is to be administered to a subject, a beneficial course of action is to first identify the CYP2C19 genotype of that subject, and then using the genotype information as the basis for determining an effective dose of the inhibitor which is appropriate for that subject (Aliment. Pharmacol. Ther., 1999, Vol. 13, p453–458).

As mentioned hereinabove, some existing proton pump inhibitors induce enzymes of the CYP1A family. When enzyme induction occurs, pharmacological activities of theophylline, caffeine, and similar drugs which are metabolized by these enzymes are lost at an early stage, inviting the risk of drug interaction in which the intended therapeutic effect cannot be obtained (Eur. J. Clin. Pharmacol., 1995, Vol. 48, p391–395).

It is also known that some procarcinogens are activated when they are ingested and metabolized by CYP1A subfamily members, and thereby exhibit carcinogenicity. Thus, conceivably, when administration of a proton pump inhibitor that can induce a member isoform of the CYP1A family in fact results in induction of the isoform, activation of the procarcinogens is promoted, raising the risk of increased cancer incidence (Gastroenterology, 1990, Vol. 99, p737–747).

Because of these factors, there has been a demand for proton pump inhibitors which, without being affected by enzyme activity of CYP2C19, will ensure that patients who receive the inhibitors can equally enjoy proper therapeutic effects at the same dose and which, due to the absence of induction of members of the CYP1A family, have low risk of inducing drug interaction attributed to the increase in the enzymatic activities of such members, as well as low risk of developing cancer.

DISCLOSURE OF THE INVENTION

In view of the foregoing, the present inventors have synthesized numerous compounds, and performed screening by use of a comprehensive screening method they have devised; that is, a screening method using, as indices, all of the proton pump inhibitory action, CYP2C19 activity inhibiting ability, and CYP1A2-inducing ability, and have found that the benzimidazole derivative of the following formula (1) or a salt thereof exhibit excellent proton pump inhibitory action, are less metabolized by CYP2C19, and have low CYP1A2-inducing ability, and therefore exhibit minimized differences in therapeutic effects among patients and are highly safe, and are thus useful as peptic ulcer remedies, leading to completion of the invention.

Accordingly, the present invention provides a benzimidazole derivative of the following formula (1):

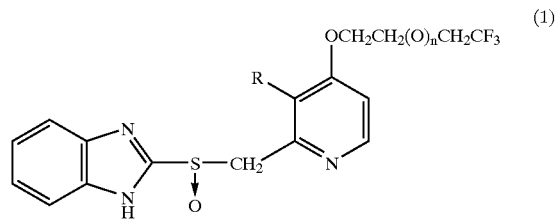

(1)

(wherein R represents a hydrogen atom or a methoxy group, and n is 0 or 1) or a salt thereof.

The present invention also provides a medicament containing as an active ingredient a benzimidazole derivative of formula (1) or a salt thereof.

The present invention also provides a medicinal composition containing a benzimidazole derivative of formula (1) or a salt thereof and a pharmacologically acceptable carrier therefor.

The present invention also provides a method for inhibiting gastric acid secretion and a method for treating peptic ulcer, characterized by administering a benzimidazole derivative of formula (1) or a salt thereof.

The present invention also provides use of a benzimidazole derivative of formula (1) or a salt thereof for producing a medicament.

BEST MODE FOR CARRYING OUT THE INVENTION

No particular limitations are imposed on the salts of the compound of the present invention, so long as the salts are pharmacologically acceptable. Examples of the salts include acid-addition salts of inorganic acid, such as hydrochloride, sulfate, nitrate, phosphate, hydrobromide, and hydroiodide; addition salts of organic acid, such as acetate, oxalate, malonate, succinate, maleate, fumarate, lactate, malate, citrate, tartrate, methanesulfonate, ethanesulfonate, and tetrafluoroborate; and metallic salts such as lithium salt, sodium salt, potassium salt, calcium salt, magnesium salt, and bismuth salt.

Specific examples of a compound of the present invention in which R is a methoxy group include 2-[3-methoxy-4-(4, 4,4-trifluorobutoxy)pyridin-2-yl-methanesulfinyl]-1H-benzimidazole, 2-{3-methoxy-4-[2-(2,2,2-trifluoroethoxy) ethoxy]pyridin-2-yl-methanesulfinyl}-1H-benzimidazole, (+)-2-[3-methoxy-4-(4,4,4-trifluorobutoxy) pyridin-2-yl-methanesulfinyl]-1H-benzimidazole, (+)-2-{3-methoxy-4-[2-(2,2,2-trifluoroethoxy) ethoxy]pyridin-2-yl-methanesulfinyl}-1H-benzimidazole, (−)-2-[3-methoxy-4-(4,4,4-trifluorobutoxy) pyridin-2-yl-methanesulfinyl]-1H-benzimidazole, (−)-2-{3-methoxy-4-[2-(2,2,2-trifluoroethoxy) ethoxy]pyridin-2-yl-methanesulfinyl}-1H-benzimidazole, and salts thereof.

Specific examples of a compound of the present invention in which R is a hydrogen atom include 2-[4-(4,4,4-trifluorobutoxy) pyridin-2-yl-methanesulfinyl]-1H-benzimidazole, 2-{4-[2-(2,2,2-trifluoroethoxy)ethoxy] pyridin-2-yl-methanesulfinyl}-1H-benzimidazole, (+)-2-[4-(4,4,4-trifluorobutoxy) pyridin-2-yl-methanesulfinyl]-1H-benzimidazole, (+)-2-{4-[2-(2,2,2-trifluoroethoxy) ethoxy] pyridin-2-yl-methanesulfinyl}-1H-benzimidazole, (−)-2-[4-(4,4,4-trifluorobutoxy) pyridin-2-yl-methanesulfinyl]-1H-benzimidazole, (−)-2-{4-[2-(2,2,2-trifluoroethoxy) ethoxy] pyridin-2-yl-methanesulfinyl}-1H-benzimidazole, and salts thereof.

The compounds of the present invention may have stereoisomers, and optically active compounds and racemic compounds fall within the scope of the present invention. In addition, the compounds of the present invention encompass solvates lead by hydrates.

The compounds of the present invention may be produced through any of the following process 1 or 2:

(Production Process 1)

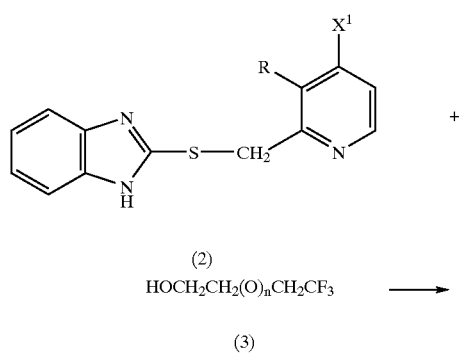

(2)

HOCH$_2$CH$_2$(O)$_n$CH$_2$CF$_3$ ⟶

(3)

-continued

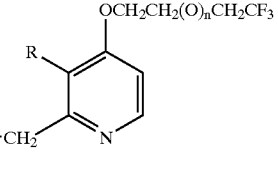

(4)

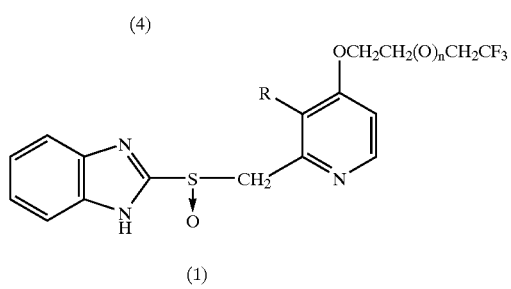

(1)

(wherein X$^1$ represents a halogen atom, and n and R have the same meanings as described above.)

Briefly, a 4-halogenopyridine (2) and an alcohol (3) are subjected to condensation reaction in the presence of a base. Subsequently, the resultant methylthiobenzimidazole (4) is oxidized, to thereby obtain a compound (1) of the present invention.

Starting material 4-halogenopyridine (2) is obtained, for example, through reaction between 4-chloro-2-chloromethyl-3-methoxypyridine and 1H-benzimidazole-2-thiol performed in the presence of a base such as sodium hydroxide.

Examples of the base employed in the condensation reaction between 4-halogenopyridine (2) and alcohol (3) include a metal hydride such as sodium hydride, lithium hydride, or potassium hydride; a metal such as lithium, sodium, or potassium; potassium t-butoxide; and n-butyllithium. The condensation reaction is preferably performed in a solvent such as dimethyl sulfoxide, N,N-dimethylformamide, dimethoxyethylene, tetrahydrofuran, or dioxane, or in alcohol (3), which serves as a solvent, at a temperature between room temperature and reflux temperature for 1 to 24 hours under stirring.

The oxidation reaction of the resultant methylthiobenzimidazole (4) is preferably performed by use of, among others, an organic peracid such as m-chloroperbenzoic acid or peracetic acid; an alcohol peroxide such as sodium metaperiodate, cumene hydroxyperoxide, t-butoxy peroxide, or aqueous hydrogen peroxide; or OXONE (product of Du Pont). The oxidation reaction is preferably performed in a solvent such as methylene chloride, chloroform, N,N-dimethylformamide, toluene, or ethyl acetate at 0 to 50° C. for 10 minutes to 24 hours under stirring.

(Production Process 2)

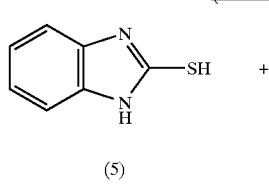

(5)

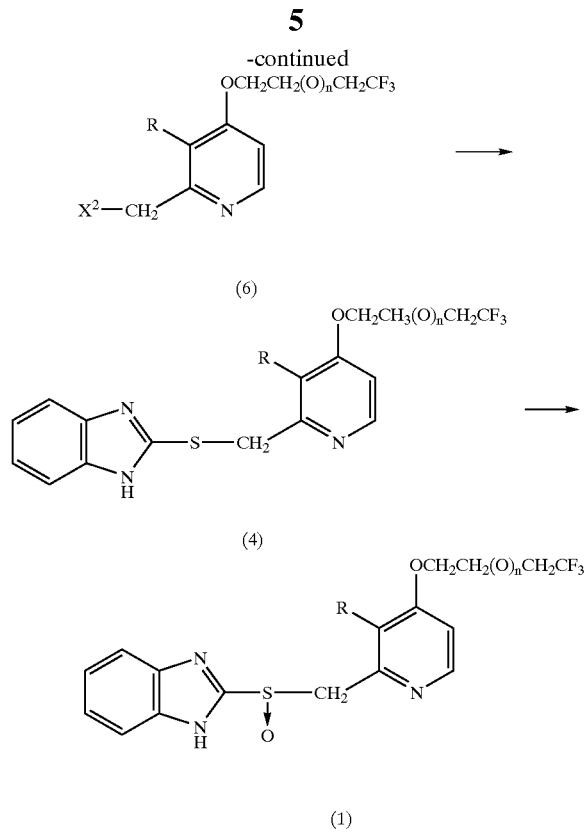

(wherein $X^2$ represents a hydroxy group or a halogen atom, and n and R have the same meanings as described above.)

Briefly, 1H-benzimidazole-2-thiol (5) is reacted with a 2-substituted methylpyridine (6). Subsequently, the resultant methylthiobenzimidazole (4) is oxidized, to thereby obtain a compound (1) of the present invention. In the case in which $X^2$ of the compound (6) is a hydroxy group, prior to performing the present reaction scheme, the compound (6) is treated with a halogenating agent such as thionyl chloride.

Examples of a base employed in the reaction between 1H-benzimidazole-2-thiol (5) and 2—substituted methylpyridine (6) include sodium hydroxide, lithium hydroxide, and potassium hydroxide. Examples of a solvent employed in the reaction include an alcohol such as methanol, ethanol, or a hydrated alcohol thereof; an aprotic solvent such as dimethyl sulfoxide or N,N-dimethylformamide; and an ether such as tetrahydrofuran or dioxane. The reaction is preferably performed at a temperature between room temperature and reflux temperature for 1 to 24 hours under stirring.

The oxidation reaction of the resultant methylthiobenzimidazole (4) is performed in a manner similar to that described in relation to the above Production Process 1.

When the compound of the present invention to be produced is an optically active compound, the oxidation reaction is performed through use of N,N-diisopropylethylamine, titanium tetraisopropoxide, or an optically active hydroxycalboxylic acid ester (e.g., a tartaric acid ester or a mandelic acid ester (which is suitably selected from among the L-form and D-form so as to produce a desired optically active compound)) and alcohol peroxide (Sharpless oxidation), to thereby obtain a desired optically active compound of the present invention.

The resultant compound (1) of the present invention may be transformed into a desired salt through a routine method by use of an alkali such as sodium hydroxide or potassium hydroxide. The salt may further be transformed into another salt through salt exchange by use of, for example, magnesium chloride or calcium chloride (and an alcohol, which serves as a solvent, particularly, ethanol or hydrated ethanol).

The compound (1) of the present invention exhibits excellent proton pump inhibitory action and gastric-acid secretion inhibition activity, is quantitatively less metabolized by human CYP2C19, and has low CYP1A2—inducing ability. Therefore, the compound (1) of the present invention, due to minimized difference in therapeutic effect between subjects, which difference would otherwise be derived from different CYP2C19 activity from subject to subject, ensures that all patients can enjoy proper therapeutic effects at the same dose of the drug. Also, the compound (1) of the present invention has low risk of drug interaction caused by induction of CYP1A family member enzymes as well as low risk of development of cancer, and thus is useful as a gastric-acid secretion inhibitor or a remedy for peptic ulcer, reliably providing therapeutic effects with safety.

The medicament of the present invention contains as an active ingredient a compound (1) of the present invention or salts thereof, and may be formed into a medicinal composition containing a compound (1) of the present invention or salts thereof and a pharmacologically acceptable carrier therefor.

When the compound of the present invention is administered as a gastric-acid secretion inhibitor or a remedy for peptic ulcer, the compound may be perorally administered in the form of granule, powder, capsule, or syrup, or parenterally administered in the form of suppository, injection, external preparation, or instillation. The dose of the compound of the present invention depends on the severity of condition, the patient's age, and the type of ulcer. Generally, the daily dose is about 0.01 to 200 mg, preferably 0.05 to 50 mg, more preferably 0.1 to 10 mg, and the compound is to be administered once a day or several times a day in a divided manner.

Drug products of the compound of the present invention are produced through a routine method by use of a conventional carrier.

A solid drug product for oral administration is prepared as follows. The active ingredient is mixed with an excipient (and, if necessary, an additive such as a binder, a disintegrant, a lubricant, a coloring agent, or a sweetening/flavoring agent), and the resultant mixture is processed through a routine method, to thereby produce a product in the form of, for example, tablets, coated tablets, granules, powder, or capsules.

Examples of the excipient include lactose, corn starch, saccharose, glucose, sorbitol, crystalline cellulose, silicon dioxide; examples of the binder include poly(vinyl alcohol), poly(vinyl ether), ethyl cellulose, methyl cellulose, acacia, tragacanth, gelatin, shellac, hydroxypropyl cellulose, hydroxypropyl starch, and poly(vinylpyrrolidone); examples of the disintegrant include starch, agar, gelatin powder, crystalline cellulose, calcium carbonate, sodium hydrogencarbonate, calcium citrate, dextrin, and pectin; examples of the lubricant include magnesium stearate, talc, polyethylene glycol, silica, and hydrogenated vegetable oil; examples of the coloring agent include coloring agents that is permitted to add medicinal products; and examples of the sweetening and flavoring agent include cocoa powder, menthol, aromatic powder, mentha oil, borneol, and powdered cinnamon bark. These oral solid drug products may be formed in an enteric drug product through use of coating materials such as hydroxypropylmethylcellulose phthalate, hydroxypropylmethylcellulose acetate succinate, cellulose acetate phthalate, and methacrylate copolymer. Needless to say, these tablets or granules may be suitably coated with sugar, gelatin, or other coating materials, according to needs.

An injection is prepared as follows. The active ingredient, which has been mixed with, if necessary, an additive such as a pH regulator, a buffer, a stabilizer, or a solubilizer, is processed through a routine method, to thereby produce an injection such as a subcutaneous injection, an intramuscular injection, or an intravenous injection.

EXAMPLES

The present invention will next be described in more detail by way of examples, which should not be construed as limiting the invention thereto.

Referential Example 1

(1) Acetic anhydride (400 mL) was added to 4-chloro-3-methoxy-2-methylpyridine-1-oxide (65.0 g), and the mixture was heated at 90° C. About three minutes thereafter, vigorous reaction was started, and the reaction was completed in 20 minutes. The solvent was removed under reduced pressure. Subsequently, toluene (50 mL) was added to the residue, and the solvent was removed under reduced pressure. The residual oil was employed in the following reaction.

(2) The residue obtained in (1) was dissolved in methanol (200 mL), and a solution prepared by dissolving 85% potassium hydroxide (50.0 g) in 100 mL water was added to the mixture with stirring under cooling with an ice bath. The ice bath was removed, and stirring was continued at room temperature for 30 minutes. The reaction mixture was concentrated under reduced pressure (bath temperature: 40° C.), and water (400 mL) was added thereto, followed by extraction with methylene chloride (200 mL×3). Subsequently, combined organic layers were washed with brine, followed by dehydration over sodium sulfate anhydrate. The solvent was removed under reduced pressure. The residue was washed with a small amount of a hexane-isopropyl ether mixture, whereby 4-chloro-2-hydroxymethyl-3-methoxypyridine was obtained (46.1 g, yield: 71%).
$^1$H-NMR(CDCl$_3$, δ):
3.89 (3H, s), 4.00 (1H, t, J=5.0 Hz), 4.80 (2H, d, J=5.0 Hz), 7.30 (1H, d, J=5.5 Hz), 8.23 (1H, d, J=5.5 Hz)
m.p.: 68–69° C.

(3) 4-Chloro-2-hydroxymethyl-3-methoxypyridine (41.0 g) was dissolved in methylene chloride (150 mL), and thionyl chloride was added dropwise over 10 minutes with stirring under cooling with an ice bath. The ice bath was removed, and the mixture was stirred for 30 minutes at room temperature. The solvent was removed under reduced pressure, and hexane (50 mL) was added to the residue, followed by distillation, whereby 4-chloro-2-chloromethyl-3-methoxypyridine chloride was obtained as a brown solid (54.1 g, yield: quantitative).

(4) 4-Chloro-2-chloromethyl-3-methoxypyridine chloride (54.1 g) was dissolved in ethanol (200 mL), and 1H-benzimidazole-2-thiol (35.4 g) was added. A solution prepared by dissolving 18.9 g sodium hydroxide in 300 mL water was added dropwise thereto under cooling with an ice bath over 30 minutes. The mixture was stirred under cooling with an ice bath for 30 minutes. The crystalline solid so precipitated was collected through filtration, followed by washing with water. After removal of water, the solid was dissolved in methylene chloride, and the organic layer was separated. The organic layer was washed with water and brine, followed by dehydration over sodium sulfate anhydrate. The solvent was removed under reduced pressure. The residue was subjected to silica gel column chromatography (silica gel: NH-DM1020 (product of Fuji Silicia), methylene chloride), whereby 2-[(4-chloro-3-methoxy)pyridin-2-yl-methylthio]-1H-benzimidazole was obtained (62.7 g, yield: 86.9%).
$^1$H-NMR(CDCl$_3$, δ):
4.00 (3H, s), 4.47 (2H, s), 7.15–7.22 (2H, m), 7.37 (1H, d, J=5.5 Hz), 7.42–7.65 (2H, m), 8.29 (1H, d, J=5.5 Hz), 12.20–12.30 (1H, bs)
m.p. : 140–141° C.
MASS(El): 305M$^+$ Referential Example 2

4,4,4-Trifluorobutanol was added dropwise to a suspension of 234 mg sodium hydride (60% dispersion in oil) in 5 mL dimethyl sulfoxide under cooling with an ice bath. After completion of addition, the mixture was stirred for two hours at room temperature. 2-[(4-Chloro-3-methoxy)pyridin-2-yl-methylthio]-1H-benzimidazole (600 mg) was added to the reaction mixture. The mixture was heated to 60° C. (internal temperature) and stirred for two hours. The reaction mixture was poured on to crushed ice and water (50 mL), and saturated potassium hydrogensulfate solution was added until the pH of the mixture became 7, followed by extraction with ethyl acetate (30 mL×2). Organic layers were combined, washed sequentially with water and brine, and brought to dryness over sodium sulfate anhydrate. The solvent was removed under reduced pressure. The crystals thus produced were washed with n-hexane-isopropyl ether mixture, whereby 2-[3-methoxy-4-(4,4,4-trifluorobutoxy)pyridin-2-yl-methylthio]-1H-benzimidazole was obtained (580 mg, yield: 74.5%).
$^1$H-NMR(CDCl$_3$, δ):
2.11–2.41 (4H, m), 3.94 (3H, s), 4.16 (2H, t, J=6.5 Hz), 4.40 (2H, s), 6.84 (1H, d, J=5.5 Hz), 7.17–7.22 (2H, m), 7.53–7.57 (2H, m), 8.26 (1H, d, J=5.5 Hz), 12.70–12.80 (1H, bs)
MASS(El): 397M$^+$ Example 1

(1) A 20 mL solution of 80% m-chloroperbenzoic acid (309 mg) in methylene chloride was added dropwise to a mixture of 2-[3-methoxy-4-(4,4,4-trifluorobutoxy)pyridin-2-yl-methylthio]-1H-benzimidazole (580 mg) in a solvent mixture of methylene chloride (5 mL) and dimethylformamide (25 mL) over 20 minutes under cooling with an ice bath. After completion of addition, the mixture was stirred for 50 minutes at the same temperature. The reaction mixture was poured on to a 50-mL crushed ice and saturated sodium bicarbonate solution, followed by extraction with ethyl acetate (30 mL×2). Organic layers were combined, washed twice with water and with brine, and subsequently brought to dryness over sodium sulfate anhydrate. The solvent was removed under reduced pressure. The residue was subjected to silica gel column chromatography (silica gel: NH-DM1020 (product of Fuji Silicia), chloroform:methanol=20:1), whereby 2-[3-methoxy-4-(4,4,4-trifluorobutoxy)pyridin-2-yl-methylsulfinyl]-1H-benzimidazole was obtained (524 mg, yield: 89%).

(2) The thus-obtained 2-[3-methoxy-4-(4,4,4-trifluorobutoxy) pyridin-2-yl-methylsulfinyl]-1H-benzimidazole (524 mg) was dissolved in an aqueous 0.1N sodium hydroxide solution (12.7 mL) and ethanol (3 mL). The solvent was removed under reduced pressure. Ether was added to the resultant powder. The powder that precipitated was collected by filtration, followed by drying under reduced pressure at room temperature, whereby a sodium salt of 2-[3-methoxy-4-(4,4,4-trifluorobutoxy) pyridin-2-yl-methylsulfinyl]-1H-benzimidazole was obtained (498 mg, yield: 90%).
$^1$H-NMR(DMSO-d$_6$, δ):
1.95–2.05 (2H, m), 2.40–2.50 (2H, m), 3.81 (3H, s), 4.18 (2H, t, J=6.5 Hz), 4.32 (1H, d, J=13.0 Hz), 4.74 (1H, d, J=13.0 Hz), 6.84–6.88 (2H, m), 7.07 (1H, d, J=5.5 Hz), 7.43–7.47 (2H, m), 8.21 (1H, d, J=5.5 Hz)
MASS(FAB): 436 MH$^+$
IR(KBr, cm$^{-1}$): 3450, 1589, 1387, 1255, 1151, 1035

Referential Example 3

2,2,2-Trifluoroethanol (24.0 g), triethylamine (24.0 g), tetrabutylammonium iodide (1.7 g), and ethylene carbonate (30.5 g) were mixed, and the mixture was heated at 100° C. (internal temperature) and stirred for 36 hours. The reaction mixture was concentrated under reduced pressure at room temperature, and then subjected by distillation (67° C., 30 mmHg), whereby 2-(2,2,2-trifluoroethoxy)ethanol was obtained (24.7 g, yield: 71%).
$^1$H-NMR(CDCl$_3$, δ):
1.97–1.99 (1H, m), 3.73–3.78 (4H, m), 3.90 (2H, q, J=8.5 Hz)

Referential Example 4

2-(2,2,2-Trifluoroethoxy)ethanol (3.77 g) was added dropwise to a suspension of 785 mg sodium hydride (60% dispersion in oil) in 20 mL dimethyl sulfoxide under cooling with an ice bath. After completion of addition, the mixture was heated to 50° C. and stirred for 30 minutes. 2-[(4-Chloro-3-methoxy) pyridin-2-yl-methylthio]-1H-benzimidazole (2.0 g) was added to the reaction mixture, and stirring was continued for 1.5 hours at 50° C. The reaction mixture was added to crushed ice and water (50 mL), followed by extraction with ethyl acetate (100 mL). The organic layer was washed sequentially with water and brine, and brought to dryness over sodium sulfate anhydrate. The solvent was removed under reduced pressure. The residue was subjected to silica gel column chromatography (hexane:ethyl acetate=1:2), whereby 2-{3-methoxy-4-[2-(2,2,2-trifluoroethoxy)ethoxy]pyridin-2-yl-methylthio}-1H-benzimidazole was obtained as an oil (2.0 g, yield: 74%).
$^1$H-NMR(CDCl$_3$, δ):
3.96 (3H, s), 3.97 (2H, q, J=8.5 Hz), 4.05–4.08 (2H, m), 4.26–4.29 (2H, m), 4.40 (2H, s), 6.86 (1H, d, J=5.5 Hz), 7.17–7.21 (2H, m), 7.40–7.70 (2H, m), 8.27 (1H, d, J=5.5 Hz), 12.80–12.90 (1H, bs)
MASS(EI): 413M$^+$ Example 2

(1) A 10 mL solution of 80% m-chloroperbenzoic acid (329 mg) in methylene chloride was added dropwise to a solution of 2-{3-methoxy-4-[2-(2,2,2-trifluoroethoxy) ethoxy]pyridin-2-yl-methylthio}-1H-benzimidazole in 10 mL methylene chloride over 20 minutes under cooling with an ice bath. After completion of addition, the mixture was stirred for 60 minutes at the same temperature. The reaction mixture was poured on to a 50-mL crushed ice and saturated sodium bicarbonate solution, followed by extraction with chloroform (40 mL×2). Organic layers were combined, washed twice with water and once with brine, and subsequently brought to dryness over sodium sulfate anhydrate. The solvent was removed under reduced pressure. The residue was subjected to silica gel column chromatography (silica gel: NH-DM1020 (product of Fuji Silicia), chloroform:methanol=20:1), whereby 2-{3-methoxy-4-[2-(2,2,2-trifluoroethoxy)ethoxy]pyridin-2-yl-methylsulfinyl}-1H-benzimidazole was obtained (560 mg, yield: 86%).

(2) The thus-obtained 2-{3-methoxy-4-[2-(2,2,2-trifluoroethoxy)ethoxy]pyridin-2-yl-methylsulfinyl}-1H-benzimidazole (560 mg) was dissolved in 0.1N sodium hydroxide solution (13.0 mL) and ethanol (3 mL). The solvent was removed under reduced pressure. Ether was added and resultant precipitate was collected by filtration, followed by drying under reduced pressure at room temperature, whereby a sodium salt of 2-{3-methoxy-4-[2-(2,2,2-trifluoroethoxy)ethoxy]pyridin-2-yl-methylsulfinyl}-1H-benzimidazole was obtained (523 mg, yield: 89%).
$^1$H-NMR(DMSO-d$_6$, δ):
3.81 (3H, s), 3.95–4.00 (2H, m), 4.17 (2H, q, J=9.0 Hz), 4.25–4.30 (2H, m), 4.35 (1H, d, J=13.0 Hz), 4.72 (1H, d, J=13.0 Hz), 6.80–6.90 (2H, m), 7.08 (1H, d, J=5.5 Hz), 7.40–7.50 (2H, m), 8.20 (1H, d, J=5.5 Hz)
MASS(FAB): 452 MH$^+$
IR(KBr, cm$^{-1}$): 2943, 1589, 1492, 1269, 1163, 1074, 1010

Example 3

(1) 2-{3-Methoxy-4-[2-(2,2,2-trifluoroethoxy)ethoxy] pyridin-2-yl-methylthio}-1H-benzimidazole (1.56 g) was dissolved in anhydrous toluene (40 mL). Water (68 μL) and Molecular Sieve 4A (1.5 g) were added, and the mixture was stirred for 15 minutes at room temperature. Subsequently, diethyl L-(+)-tartrate (1.95 g) and tetraisopropyl titanate (1.07 g) were sequentially added, and the mixture was stirred for one hour at 50° C. The temperature of the mixture was returned to room temperature. N,N-Diisopropylethylamine (650 μL) and cumene hydroxyperoxide (560 μL) were added, and the mixture was stirred for further three hours at room temperature. Saturated sodium sulfite solution (4 mL) was added to the reaction mixture, and the mixture was stirred for 10 minutes, followed by filtration. Saturated sodium hydrogencarbonate solution was added to the filtrate, and the mixture was stirred, followed by filtration through the Celite. The filtrate was extracted with toluene. The organic layer was washed sequentially with water and brine, and brought to dryness with sodium sulfate anhydrate. The solvent was removed under reduced pressure. The residue was subjected to silica gel column chromatography (silica gel: NH-DM1020 (product of Fuji Silicia), chloroform:methanol=20:1), whereby (+)-2-{3-methoxy-4-[2-(2,2,2-trifluoroethoxy) ethoxy]pyridin-2-yl-methylsulfinyl}-1H-benzimidazole was obtained (1.13 g).

(2) (+)-2-{3-Methoxy-4-[2-(2,2,2-trifluoroethoxy) ethoxy]pyridin-2-yl-methylsulfinyl}-1H-benzimidazole (1.13 g) was dissolved in acetonitrile (5 mL). An aqueous 0.1N sodium hydroxide solution (26.2 mL) was added, and the mixture was stirred. The solvent was removed under reduced pressure, and the residue was subjected to recrystallization with diethyl ether, whereby a sodium salt of (+)-2-{3-methoxy-4-[2-(2,2,2-trifluoroethoxy) ethoxy] pyridin-2-yl-methylsulfinyl}-1H-benzimidazole was obtained (880 mg).
$^1$H-NMR(DMSO-d$_6$, δ):
3.81 (3H, s), 3.99–4.01 (2H, m), 4.18 (2H, q, J=9.0 Hz), 4.27–4.38 (2H, m), 4.33 (1H, d, J=13.0 Hz), 4.72 (1H, d, J=13.0 Hz), 6.85–6.88 (2H, m), 7.08 (1H, d, J=5.5 Hz), 7.44–7.47 (2H, m), 8.20 (1H, d, J=5.5 Hz)
MASS(FAB): 452 MH$^+$
Optical purity: 89.7% ee (liquid chromatography)
$[α]D^{25}$=+39.4 (c=0.51, H$_2$O)

Example 4

The procedure of Example 3 was repeated, except that diethyl D-(−)-tartrate was used instead of diethyl L-(+)-tartrate, to thereby obtain a sodium salt of (−)-2-{3-methoxy-4-[2-(2,2,2-trifluoroethoxy) ethoxy]pyridin-2-yl-methylsulfinyl}-1H-benzimidazole.

$^1$H-NMR(DMSO-$d_6$, δ):
3.80 (3H, s), 3.98–4.01 (2H, m), 4.18 (2H, q, J=9.0 Hz), 4.25–4.38 (2H, m), 4.34 (1H, d, J=13.0 Hz), 4.72 (1H, d, J=13.0 Hz), 6.85–6.87 (2H, m), 7.09 (1H, d, J=5.5 Hz), 7.44–7.47 (2H, m), 8.20 (1H, d, J=5.5 Hz)
MASS(FAB): 452 MH$^+$
Optical purity: 92.0% ee (liquid chromatography)
$[α]D^{25}$=−39.5 (c=0.500, $H_2O$)

Example 5

(1) The general procedure of Example 3 was repeated by use of 2-[3-methoxy-4-(4,4,4-trifluorobutoxy)pyridin-2-yl-methylthio]-1H-benzimidazole obtained in Referential Example 2 as a raw material, to thereby obtain a sodium salt of (+)-2-[3-methoxy-4-(4,4,4-trifluorobutoxy)pyridin-2-yl-methanesulfinyl]-1H-benzimidazole.

$^1$H-NMR(DMSO-$d_6$, δ):
1.95–2.05 (2H, m), 2.40–2.50 (2H, m), 3.81 (3H, s), 4.18 (2H, t, J=6.5 Hz), 4.34 (1H, d, J=13.0 Hz), 4.74 (1H, d, J=13.0 Hz), 6.86–6.89 (2H, m), 7.07 (1H, d, J=5.5 Hz), 7.44–7.48 (2H, m), 8.20 (1H, d, J=5.5 Hz)
MASS(FAB): 436 MH$^+$
Optical purity: 75.9% ee (liquid chromatography)
$[α]D^{25}$=+66.7 (c=0.500, MeOH)

(2) A sodium salt of (+)-2-[3-methoxy-4-(4,4,4-trifluorobutoxy)pyridin-2-yl-methanesulfinyl]-1H-benzimidazole (2.0 g) was dissolved in a mixture of 20 mL methanol and 40 mL water. A solution of 467 mg magnesium chloride hexahydrate in 10 mL water was added thereto at room temperature, and the mixture was stirred for 30 minutes. The precipitates were collected through filtration, followed by drying under reduced pressure, whereby a magnesium salt of (+)-2-[3-methoxy-4-(4,4,4-trifluorobutoxy)pyridin-2-yl-methanesulfinyl]-1H-benzimidazole was obtained (1.03 g).

$^1$H-NMR(CD$_3$OD, δ):
1.98–2.05 (2H, m), 2.24–2.31 (2H, m), 3.69 (3H, s), 4.10 (2H, t, J=6.0 Hz), 4.65–4.75 (2H, m), 6.97 (1H, d, J=5.5 Hz), 7.04–7.10 (2H, m), 7.40–7.50 (2H, m), 8.02 (1H, d, J=5.5 Hz)
$[α]D^{25}$=+113.4 (c=0.520, MeOH)
MASS(FAB): 849 MH$^+$

Example 6

(1) The procedure of Example 3 was repeated, except that 2-[3-methoxy-4-(4,4,4-trifluorobutoxy)pyridin-2-yl-methylthio]-1H-benzimidazole obtained in Referential Example 2 was used as a raw material and that diethyl D-(−)-tartrate was used instead of diethyl L-(+)-tartrate, to thereby obtain a sodium salt of (−)-2-[3-methoxy-4-(4,4,4-trifluorobutoxy)pyridin-2-yl-methanesulfinyl]-1H-benzimidazole.

$^1$H-NMR(DMSO-$d_6$, δ):
1.95–2.05 (2H, m), 2.40–2.50 (2H, m), 3.81 (3H, s), 4.18 (2H, t, J=6.5 Hz), 4.32 (1H, d, J=13.0 Hz), 4.78 (1H, d, J=13.0 Hz), 6.85–6.88 (2H, m), 7.06 (1H, d, J=5.5 Hz), 7.44–7.47 (2H, m), 8.20 (1H, d, J=5.5 Hz)
MASS(FAB): 436 MH$^+$
Optical purity: 82.0% ee (liquid chromatography)
$[α]D^{25}$=−73.3 (c=0.468, MeOH)

(2) The general procedure of Example 5 (2) was repeated by use of a sodium salt of (−)-2-[3-methoxy-4-(4,4,4-trifluorobutoxy) pyridin-2-yl-methanesulfinyl]-1H-benzimidazole, to thereby obtain a magnesium salt of (−)-2-[3-methoxy-4-(4,4,4-trifluorobutoxy) pyridin-2-yl-methanesulfinyl]-1H-benzimidazole.

$^1$H-NMR(CD$_3$OD, δ):
1.97–2.03 (2H, m), 2.23–2.32 (2H, m), 3.67 (3H, s), 4.09 (2H, t, J=6.0 Hz), 4.65–4.75 (2H, m), 6.95 (1H, d, J=5.5 Hz), 6.95–7.05 (2H, m), 7.40–7.50 (2H, m), 8.01 (1H, d, J=5.5 Hz)
$[α]D^{25}$=−115.5 (c=0.496, MeOH)
MASS(FAB): 849 MH$^+$

Example 7

The general procedure of Example 5 (2) was repeated by use of a sodium salt of (+)-2-{3-methoxy-4-[2-(2,2,2-trifluoroethoxy) ethoxy]pyridin-2-yl-methylsulfinyl}-1H-benzimidazole, to thereby obtain a magnesium salt of (+)-2-{3-methoxy-4-[2-(2,2,2-trifluoroethoxy) ethoxy]pyridin-2-yl-methylsulfinyl}-1H-benzimidazole.

$^1$H-NMR(CD$_3$OD, δ):
3.71 (3H, s), 3.93 (2H, q, J=9.0 Hz), 3.92–3.95 (2H, m), 4.18–4.21 (2H, m), 4.76–4.80 (2H, m), 6.97 (1H, d, J=5.5 Hz), 6.99–7.05 (2H, m), 7.40–7.50 (2H, m), 8.01 (1H, d, J=5.5 Hz)
$[α]D^{25}$=+44.0 (c=0.502, $H_2O$)
MASS(FAB): 881 MH$^+$

Example 8

The general procedure of Example 5 (2) was repeated by use of a sodium salt of (−)-2-{3-methoxy-4-[2-(2,2,2-trifluoroethoxy) ethoxy]pyridin-2-yl-methylsulfinyl}-1H-benzimidazole, to thereby obtain a magnesium salt of (−)-2-{3-methoxy-4-[2-(2,2,2-trifluoroethoxy) ethoxylpyridin-2-yl-methylsulfinyl}-1H-benzimidazole.

$^1$H-NMR(CD$_3$OD, δ):
3.70 (3H, s), 3.92 (2H, q, J=9.0 Hz), 3.90–3.93 (2H, m), 4.15–4.21 (2H, m), 4.77–4.82 (2H, m), 6.97 (1H, d, J=5.5 Hz), 6.98–7.05 (2H, m), 7.40–7.50 (2H, m), 8.01 (1H, d, J=5.5 Hz)
$[α]D^{25}$=−44.0 (c=0.506, $H_2O$)
MASS(FAB): 881 MH$^+$

Example 9

(1) 2-Hydroxymethyl-4-(4,4,4-trifluorobutoxy)pyridine (9.6 g) was dissolved in methylene chloride (100 mL). Thionyl chloride (5.3 g) was added dropwise under cooling with an ice bath, and the mixture was stirred for 30 minutes at the same temperature. The mixture was concentrated under reduced pressure, and the residue was dissolved in methanol (100 mL). 2-Mercaptobenzimidazole (6.1 g), sodium hydroxide (4.9 g), and water (50 mL) were added thereto, and the mixture was stirred for an hour at room temperature. The reaction mixture was concentrated under reduced pressure, followed by extraction with ethyl acetate. The organic layer was washed sequentially with water and brine, and brought to dryness over sodium sulfate anhydrate. The solvent was removed under reduced pressure. The residue was subjected to silica gel column chromatography (silica gel: NH-DM1020 (product of Fuji Silicia), chloroform), whereby 2-[4-(4,4,4-trifluorobutoxy) pyridin-2-yl-methylthio]-1H-benzimidazole was obtained (13.8 g).

$^1$H-NMR(CDCl$_3$,δ):
2.07–2.15 (2H, m), 2.27–2.37 (2H, m), 4.10 (2H, t), 4.30 (2H, s), 6.80 (1H, dd), 6.88 (1H, d), 7.13–7.26 (2H, m), 7.45–7.68 (2H, m), 8.48 (1H, d), 12.91 (1H, s)

MASS(EI): 367M⁺
m.p.: 136–137° C.

(2) The thus-obtained 2-[4-(4,4,4-trifluorobutoxy) pyridin-2-yl-methylthio]-1H-benzimidazole (1.27 g) was dissolved in methylene chloride (20 mL). A solution of 80% m-chloroperbenzoic acid (746 mg) in methylene chloride (10 mL) was added dropwise at −30° C., and the mixture was stirred for an hour at the same temperature. A saturated sodium bicarbonate solution (30 mL) was added to the reaction mixture. The temperature of the mixture was returned to room temperature, and the mixture was stirred for 10 minutes, followed by extraction with methylene chloride. The organic layer was washed sequentially with water and brine, and brought to dryness over sodium sulfate anhydrate. The solvent was removed under reduced pressure. The residue was subjected to silica gel column chromatography (silica gel: NH-DM1020 (product of Fuji Silicia), chloroform:methanol=10:1), whereby 2-[4-(4,4,4-trifluorobutoxy)pyridin-2-yl-methanesulfinyl]-1H-benzimidazole was obtained (1.2 g).

(3) The thus-obtained 2-[4-(4,4,4-trifluorobutoxy) pyridin-2-yl-methanesulfinyl]-1H-benzimidazole was dissolved in ethanol (20 mL) on heating. A 5N sodium hydroxide solution (0.62 mL) was added, and then the solvent was removed under reduced pressure, whereby sodium salt of 2-[4-(4,4,4-trifluorobutoxy) pyridin-2-yl-methanesulfinyl]-1H-benzimidazole was obtained (1.2 g) as a powder.
¹H-NMR(DMSO-$d_6$, δ):
1.78–1.87 (2H, m), 2.24–2.34 (2H, m), 3.69–3.87 (2H, m), 4.44 (1H, d), 4.56 (1H, d), 6.63 (1H, d), 6.83 (1H, dd), 6.84–6.91 (2H, m), 7.44–7.48 (2H, m), 8.34 (1H, d)
MASS(FAB): 406 MH⁺

(4) The 2-[4-(4,4,4-trifluorobutoxy)pyridin-2-yl-methanesulfinyl]-1H-benzimidazole obtained in (2) was dissolved in ethanol. Potassium hydroxide solution was added, and then the solvent was removed under reduced pressure, whereby potassium salt of 2-[4-(4,4,4-trifluorobutoxy) pyridin-2-yl-methanesulfinyl]-1H-benzimidazole was obtained as a powder.
¹H-NMR(DMSO-$d_6$, δ):
1.77–1.83 (2H, m), 2.22–2.35 (2H, m), 3.60–3.70 (1H, m), 3.80–3.92 (1H, m), 4.48 (1H, d, J=12.0 Hz), 4.59 (1H, d, J=12.0 Hz), 6.61 (1H, d, J=2.5 Hz), 6.82 (1H, dd, J=2.5, 5.5 Hz), 6.86–6.89 (2H, m), 7.44–7.47 (2H, m), 8.32 (1H, d, J=5.5 Hz)
MASS(FAB): 422 MH⁺

(5) The sodium salt of 2-[4-(4,4,4-trifluorobutoxy) pyridin-2-yl-methanesulfinyl]-1H-benzimidazole obtained in (3) was subjected to salt exchange by use of magnesium chloride hexahydrate through a conventional method, whereby magnesium salt of 2-[4-(4,4,4-trifluorobutoxy) pyridin-2-yl-methanesulfinyl]-1H-benzimidazole was obtained as a powder.
¹H-NMR(DMSO-$d_6$, δ):
1.80–1.95 (2H, m), 2.30–2.45 (2H, m), 3.80–4.05 (2H, m), 4.40–4.60 (2H, m), 6.65–7.05 (4H, m), 7.45–7.55 (2H, m), 8.35–8.37 (2H, m)
MASS(FAB): 789 MH⁺

(6) The sodium salt of 2-[4-(4,4,4-trifluorobutoxy) pyridin-2-yl-methanesulfinyl]-1H-benzimidazole obtained in (3) was subjected to salt exchange by use of calcium chloride dihydrate through a conventional method, whereby calcium salt of 2-[4-(4,4,4-trifluorobutoxy)pyridin-2-yl-methanesulfinyl]-1H-benzimidazole was obtained as a powder.
¹H-NMR(DMSO-$d_6$, δ):
1.75–1.86 (2H, m), 2.25–2.31 (2H, m), 3.73–3.88 (2H, m), 4.47 (1H, d, J=12.5 Hz), 4.59 (1H, d, J=12.5 Hz), 6.67 (1H, d, J=2.5 Hz), 6.85 (1H, dd, J=2.5, 5.5 Hz), 6.90–6.94 (2H, m), 7.47–7.51 (2H, m), 8.35 (1H, d, J=5.5 Hz)
MASS(FAB): 805 MH⁺

Example 10

(1) 2-[4-(4,4,4-Trifluorobutoxy)pyridin-2-yl-methylthio]-1H-benzimidazole (6.0 g) was dissolved in ethyl acetate (150 mL). Molecular Sieve 4A (6.0 g) and water (290 μL) were added, and the mixture was stirred for 15 minutes at room temperature. Subsequently, diethyl (+)-tartrate (6.7 g) and tetraisopropyl titanate (4.6 g) were added, and the mixture was stirred for one hour at 50° C. The temperature of the mixture was returned to room temperature. N,N-Diisopropylethylamine (2.8 mL) and 88% cumene hydroxyperoxide (2.7 mL) were added, and the mixture was stirred for four hours at room temperature. A saturated sodium bicarbonate solution was added to the reaction mixture, and the mixture was stirred for 30 minutes, followed by filtration through the Celite. The filtrate was extracted with ethyl acetate. The organic layer was washed sequentially with water and brine, and brought to dryness over sodium sulfate anhydrate. The solvent was removed under reduced pressure. The residue was subjected to silica gel column chromatography (silica gel: NH-DM1020 (product of Fuji Silicia), chloroform:methanol=10:1), whereby (−)-2-[4-(4,4,4-trifluorobutoxy) pyridin-2-yl-methanesulfinyl]-1H-benzimidazole was obtained (4.5 g).

(2) The thus-obtained (−)-2-[4-(4,4,4-trifluorobutoxy) pyridin-2-yl-methanesulfinyl]-1H-benzimidazole was dissolved in ethanol (40 mL) on heating. A 5N sodium hydroxide solution (2.3 mL) was added, and then the solvent was removed under reduced pressure. The precipitates were collected through filtration, whereby sodium salt of (−)-2-[4-(4,4,4-trifluorobutoxy) pyridin-2-yl-methanesulfinyl]-1H-benzimidazole was obtained as a powder (4.7 g).
1H-NMR(DMSO-$d_6$, δ):
1.78–1.89 (2H, m), 2.22–2.40 (2H, m), 3.69–3.87 (2H, m), 4.48 (1H, d), 4.59 (1H, d), 6.69 (1H, d), 6.86 (1H, dd), 6.98–7.02 (2H, m), 7.51–7.54 (2H, m), 8.33 (1H, d)
MASS(FAB): 406 MH⁺
$[\alpha]_D^{25}$=−12.2 (c=0.48, $H_2O$)

Example 11

The procedure of Example 10 was repeated, except that diethyl (−)-tartrate was used instead of diethyl (+)-tartrate, to thereby-obtain a sodium salt of (+)-2-[4-(4,4,4-trifluorobutoxy)pyridin-2-yl-methanesulfinyl]-1H-benzimidazole.
¹H-NMR(DMSO-$d_6$, δ):
1.79–1.87 (2H, m), 2.25–2.35 (2H, m), 3.72–3.87 (2H, m), 4.45 (1H, d), 4.57 (1H, d), 6.65 (1H, d), 6.85 (1H, dd), 6.91–6.94 (2H, m), 7.47–7.50 (2H, m), 8.33 (1H,d)
MASS(FAB): 406 MH⁺
$[\alpha]_D^{25}$=+14.0 (c=0.49, $H_2O$)

Example 12

The steps of Example 9, (1) to (3) were repeated, except that 2-hydroxymethyl-4-[2-(2,2,2-trifluoroethoxy)ethoxy] pyridine was used instead of 2-hydroxymethyl-4-(4,4,4-trifluorobutoxy) pyridine, to thereby obtain a sodium salt of 2-{4-[2-(2,2,2-trifluoroethoxy) ethoxy]pyridin-2-yl-methanesulfinyl}-1H-benzimidazole.

$^1$H-NMR(DMSO-d$_6$, δ):
3.79–4.02 (4H, m), 4.07 (2H, q), 4.46 (1H, d), 4.58 (1H, d), 6.70 (1H, d), 6.84–6.89 (3H, m), 7.44–7.47 (2H, m), 8.34 (1H, d)
MASS(FAB): 422 MH$^+$

Example 13

(1) The procedure of Example 9 (1) was repeated, except that 2-hydroxymethyl-4-[2-(2,2,2-trifluoroethoxy)ethoxy] pyridine was used instead of 2-hydroxymethyl-4-(4,4,4-trifluorobutoxy)pyridine, to thereby obtain 2-{4-[2-(2,2,2-trifluoroethoxy)ethoxy]pyridin-2-yl-methylthio}-1H-benzimidazole.

(2) The thus-obtained 2-{4-[2-(2,2,2-trifluoroethoxy) ethoxy]pyridin-2-yl-methylthio}-1H-benzimidazole (6.5 g) was dissolved in toluene (160 mL). Molecular Sieve 4A (6.5 g) and water (310 μL) were added, and the mixture was stirred for 15 minutes at room temperature. Subsequently, diethyl (+)-tartrate (7.0 g) and tetraisopropyl titanate (4.8 g) were added, and the mixture was stirred for one hour at 50° C. The temperature of the mixture was returned to room temperature. N,N-Diisopropylethylamine (3.0 mL) and 88% cumene hydroxyperoxide (2.8 mL) were added, and the mixture was stirred for three hours at room temperature. A saturated sodium bicarbonate solution was added to the reaction mixture, and the mixture was stirred for 10 minutes, followed by filtration through the Celite. The filtrate was extracted with ethyl acetate. The organic layer was washed sequentially with water and brine, and brought to dryness over sodium sulfate anhydrate. The solvent was removed under reduced pressure. The residue was subjected to silica gel column chromatography (silica gel: NH-DM1020 (product of Fuji Silicia), chloroform:methanol=10:1), whereby (–)-2-{4-[2-(2,2,2-trifluoroethoxy) ethoxy]pyridin-2-yl-methanesulfinyl}-1H-benzimidazole was obtained (5.4 g).

(3) The thus-obtained (–)-2-{4-[2-(2,2,2-trifluoroethoxy) ethoxy]pyridin-2-yl-methanesulfinyl}-1H-benzimidazole was dissolved in 50 mL ethanol. A 5N sodium hydroxide solution (2.7 mL) was added, and then the solvent was removed under reduced pressure. The precipitates were collected by filtration, whereby sodium salt of (–)-2-{4-[2-(2,2,2-trifluoroethoxy) ethoxy]pyridin-2-yl-methanesulfinyl}-1H-benzimidazole was obtained as a powder (5.4 g).
$^1$H-NMR(DMSO-d$_6$, δ)
3.80–4.06 (4H, m), 4.08 (2H, q), 4.42 (1H, d), 4.57 (1H, d), 6.73 (1H, d), 6.87–6.90 (3H, m), 7.45–7.49 (2H, m), 8.35 (1H, d)
MASS(FAB): 422 MH$^+$
$[α]D^{25}$=–28.7 (c=0.49, H$_2$O)

Example 14

The steps of Example 13, (2) and (3) were repeated, except that diethyl (–)-tartrate was used instead of diethyl (+)-tartrate, to thereby obtain a sodium salt of (+)-2-{4-[2-(2,2,2-trifluoroethoxy) ethoxy]pyridin-2-yl-methanesulfinyl}-1H-benzimidazole.
$^1$H-NMR(DMSO-d$_6$, δ)
3.80–4.06 (4H, m), 4.08 (2H, q), 4.44 (1H, d), 4.58 (1H, d), 6.72 (1H, d), 6.85–6.91 (3H, m), 7.45–7.49 (2H, m), 8.35 (1H, d)
MASS(FAB): 422 MH$^+$
$[α]D^{25}$=+23.6 (c=0.49, H$_2$O)

Test Example 1

(Proton Pump Inhibitory Action)

(1) Preparation of Enzyme Sample (H$^+$/K$^+$-ATPase)

The stomach body removed from a pig, which had been stored in a frozen state, was separated into a muscle layer and a mucous membrane layer. The mucous membrane layer was homogenized in Tris-HCl buffer (20 mmol/L, pH 7.4) having a volume 5 times that of the layer and containing sucrose (0.25 mol/L) and EGTA (1 mmol/L) (hereinafter the mixture is referred to as Tris-HCl buffer) in a mixer. The homogenate was subjected to centrifugation (9,000×g, 30 minutes). The supernatant was softly placed on 8 mL Tris-HCl buffer (20 mmol/L, pH 7.4) containing 30% sucrose and 1 mmol/L EGTA. The mixture was subjected to ultracentrifugation at 100,000×g for 60 minutes. The interface fraction obtained through centrifugation was subjected to centrifugation (113,000×g, 60 minutes) twice. Pellet was suspended in Tris-HCl buffer, and the suspension was homogenized at low speed. The resultant homogenate served as an enzyme sample of interest and was stored at –80° C. The protein content of the sample was quantitated through use of a BCA protein assay reagent in accordance with a method described by Smith et al. (Anal. Biochem., 150, 76–85 (1985)). All these steps were performed under cooling with an ice bath.

(2) Activity of inhibiting H$^+$/K$^+$-ATPase (at pH 1)

Activity of inhibiting H$^+$/K$^+$-ATPase was measured in accordance with a method described in Biochem. Biophys. Res. Commun., 40, 880–886 (1970). Specifically, ATP was employed as a substrate, and inorganic phosphate, which is a resultant degradation product, was quantitated. In consideration of the solubility of test compounds, the test compounds were preliminarily treated with a hydrochloric acid solution (containing 50% DMSO, 1×10$^{-1}$ mol/L, pH 1). Each of the test compounds having different concentrations was added to the hydrochloric acid solution to thereby yield a 1,000—fold dilution, and thereafter, the diluted compound was allowed to stand for 15 minutes at room temperature. After these preliminary remedies, a 10 μL solution that had undergone the above preliminary remedies were added to 840 μL Tris-acetate buffer (40 mmol/L, pH 7.5, containing 2 mmol/L MgCl$_2$, may be referred to as TE buffer) containing or not containing 20 mmol/L KCl. Subsequently, a 100 μL enzyme solution (5 μg protein) diluted with the TE buffer was added. Incubation was performed for 30 minutes at 37° C. Thereafter, a 50 μL ATP solution (40 mmol/L) which was dissolved in TE buffer not containing KCl was added to initiate enzyme reaction (total volume: 1 mL, ATP final concentration: 2 mmol/L). Incubation was performed for 30 minutes at 37° C. Subsequently, ice-cold 12% trichloroacetic acid (2 mL) was added, to thereby stop the enzyme reaction. A molybdenum reagent (1 mL, 3.75% ammonium molybdate/1.5 mol/L sulfuric acid) and butyl acetate (5 mL) were added, followed by mixing under vigorous shaking for 5 minutes. The absorption of the butyl acetate layer was measured at 310 nm. A standard curve was determined on the basis of absorption obtained through the similar procedure by use of KH$_2$PO$_4$ at different concentrations dissolved in 8% TCA solution, and inorganic phosphate content was calculated. Samples to be measured were prepared in duplicate. The measurements were averaged, and residual activity was obtained from the difference between the inorganic phosphate content as determined in a sample containing KCl and that as determined in a sample not containing KCl. Percentage inhibition activity was calculated with respect to the activity obtained from a control sample (DMSO), which was considered 100%. As the inhibitory potency of each test compound, IC$_{50}$ values were computed and shown. All the test compounds were dissolved in dimethyl sulfoxide immediately before use.

The results are shown in Table 1.

TABLE 1

| Test compound | Proton pump inhibitory action [IC$_{50}$ (μmol/L)] |
|---|---|
| Example 1(2) | 4.16 |
| Example 2(2) | 3.37 |
| Example 3(2) | 4.05 |
| Example 4 | 3.46 |
| Example 5(1) | 3.32 |
| Example 6(1) | 2.50 |
| Example 9(3) | 3.56 |
| Example 10(2) | 3.03 |
| Example 11 | 3.77 |
| Example 12 | 7.86 |
| Example 13(3) | 7.37 |
| Example 14 | 6.67 |
| omeprazole | 1.01 |
| esomeprazole | 2.06 |
| lansoprazole | 1.61 |
| pantoprazole | 5.46 |
| rabeprazole | 1.61 |

Test Example 2
(Gastric Acid Secretion Inhibition Action)
(1) Test Animals Employed were Sprague-Dawley (SD) Rats (7 Weeks Old, Male) Purchased from Charles River Japan, Inc. Before the Test, the Rats Were Fed for 5 Days or More.

Each test drug was suspended in, or dissolved in, 0.5% sodium carboxymethylcellulose solution, whereby a suspension or solution was prepared so as to attain 2.5 mL/kg.

(2) Measurement of Gastric Acid Secretion

The amount of gastric acid secreted under stimulation with histamine was measured on the rats fasted for 18 hours by use of the acute Fistula method as described by Hiramatsu et al. (Dig. Dis. Sci.,39, 689–697(1994)). Briefly, each rat was etherized lightly, and then a winged tubular needle filled with 3.8% citric acid solution was indwelled in the tail vein of the rat. The abdomen of the rat was opened, and the pyloric part of the stomach was ligated. Subsequently, a small hole was made in the duodenum, and the abdomen of the rat was closed with a feeding tube filled with saline indwelled. The inside of the stomach was washed with saline, a polyethylene-made Fistula tube (inner diameter: 4 mm) was set in the anterior stomach, and the cut portion of the anterior stomach was ligated and secured. The stomach and the duodenum were returned to the abdominal cavity, with the Fistula tube and the feeding tube exposed outside. The rat was placed in a Ballman cage II. Histamine was continuously administered through the winged injection needle which had been indwelled in the tail vein in advance (8 mg/kg/h, 1.38 mL/h). 15 Minutes thereafter, gastric juice of the rat was collected. Subsequently, collection of gastric juice was performed every one hour. Each time, the amount of the collected gastric juice was recorded, followed by titration with NaOH (0.1 mol/L) up to the end point pH 7.0. From the volume consumed for titration, acidity was calculated. The acid discharge amount was calculated as a product of the amount of the gastric juice and the acidity. Before starting the test, the rats were grouped so that the intra-group total amount of the gastric juice samples initially collected was the same between groups. Thereafter, each test drug was administered (2.5 mL/kg) in the duodenum through a feeding tube which had been attached to the duodenum in advance. To each rat of a control group, 0.5% Na-CMC solution was administered.

(3) Analysis of the Results

The data as obtained above are shown by way of mean±standard error. Total amount of acid discharge was obtained through summation of the amounts of acid discharge at three points in time; i.e., 3, 4 and 5 hours after initial collection of gastric juice. Percent inhibition of each group was computed from the total acid discharge amount of the control group and that of each group. On the basis of the percent inhibition calculated for each group, 50% effective dose (ED$_{50}$) was computed by use of the Probit method. The results are shown in Table 2.

TABLE 2

| Test compound | Gastric-acid secretion inhibition action [ED$_{50}$ (mg/kg)] |
|---|---|
| Example 1(2) | 1.3 |
| Example 2(2) | 1.9 |
| Example 3(2) | 2.2 |
| Example 4 | 2.6 |
| Example 5(1) | 0.9 |
| Example 6(1) | 1.4 |
| Example 9(3) | 0.32 |
| Example 10(2) | 0.97 |
| Example 11 | 0.50 |
| Example 13(3) | 0.59 |
| Example 14 | 0.42 |
| omeprazole | 3.6 |
| esomeprazole | 2.9 |
| lansoprazole | 1.1 |
| pantoprazole | 0.34 |
| rabeprazole | 2.5 |

Test Example 3
(Human CYP2C19 Activity Inhibition Test)

CYP2C19 specifically participates in the metabolism reaction from S-(+)-mephenytoin to 4'-hydroxymephenytoin. Therefore, by use of an expression system CYP2C19, the production amount (concentration) of 4'-hydroxymephenytoin, serving as an index for CYP2C19 activity, was determined, whereby the inhibitory action of respective test substances was investigated.

(a) Metabolizing Activity Test

A solution of S-(+)-mephenytoin in methanol (125 μmol/L, 50 μL) and a solution of a test substance in methanol (25 μmol/L, 0, 10, 100, or 200 μL) were placed in a 10-mL glass test tube. The solvent was removed under a nitrogen gas at 40° C. A 75 μL mixture of 0.5M phosphate buffer (pH 7.4)–0.5 mM EDTA (20:10), 140 μL purified water, and 10 μL human CYP2C19 yeast expression system microsome (purchased from Sumitomo Chemical Co., Ltd.) were added. 25 μL NADPH—Generating system (a mixture of 60 mM MgCl$_2$, 6.7 mg/mL β-NADP$^+$, 27.2 mg/mL G-6-P, and 10 μL/mL G-6-Pdh) was added to initiate reaction.

Incubation was performed for 10 minutes at 37° C. Subsequently, aqueous 12% perchloric acid solution (50 μL) was added, to thereby stop the reaction.

(b) Quantitation Method

After the reaction was stopped, an internal standard substance (I.S.) methyl p-hydroxybenzoate (100 μg/ mL, 50 μL), and diethyl ether (2 mL) were added. The mixture was shaken for 10 minutes, followed by centrifugation at 3,000 rpm for 10 minutes. The organic layer was separated, and the solvent was removed under a nitrogen gas at 40° C. The residue was dissolved in a 200 μL mobile phase, and the mixture was subjected to analysis by high performance liquid chromatography (HPLC).

In order to generate a calibration curve, the general procedure of the above process was repeated by use of 4'-hydroxymephenytoin solution instead of the S-(+)-mephenytoin solution. Quantitation was performed on the basis of the peak area ratio of 4'-hydroxymephenytoin to I.S. The amount of 4'-hydroxymephenytoin generated in the control sample was compared with that generated in the present of a test compound, and the results of comparison were used as an activity index. The results obtained in the case where the concentration of the added test compound was 10 μM are shown in Table 3.

HPLC was performed under the conditions described below (HPLC conditions A or HPLC conditions B).

<Measurement Conditions>
HPLC Conditions A
  Column: CAPCELL PAK C18 UG120, 5 μm 4.6 mmϕ× 250 mm
  Precolumn: CAPCELL PAK C18 UG120, 4.0 mmϕ×10 mm
  Detection wavelength: UV 204 nm
  Detector sensitivity: 0.01 AUSF
  Mobile phase: $CH_3CN$: 50 mM phosphate buffer (pH 8)=20:80
  Flow rate of mobile phase: 0.8 mL/min
  I.S.: methyl p-hydroxybenzoate
  Column temperature: 40° C.
  Sample amount: 40 μL HPLC Conditions B
  Column: CAPCELL PAK C18 UG120, 5 μm 4.6 mmϕ× 250 mm
  Precolumn: CAPCELL PAK C18 UG120, 4.0 mmϕ×10 mm
  Detection wavelength: UV 204 nm
  Detector sensitivity: 0.01 AUSF
  Mobile phase: $CH_3CN$: 50 mM phosphate buffer (pH 4)=20:80
  Flow rate of mobile phase: 0.8 mL/min
  I.S.: methyl p-hydroxybenzoate
  Column temperature: 40° C.
  Sample amount: 40 μL

TABLE 3

| Test compound | CYP2C19 residual activity (%) |
| --- | --- |
| Example 1(2) | 71.2 |
| Example 2(2) | 66.5 |
| Example 3(2) | 98.3 |
| Example 4 | 93.9 |
| Example 5(1) | 78.6 |
| Example 6(1) | 66.4 |
| Example 9(3) | 76.1 |
| Example 10(2) | 89.4 |
| Example 12 | 88.8 |
| Example 13(3) | 98.6 |
| Example 14 | 81.4 |
| Omeprazole | 18.4 |
| Esomeprazole | 35.4 |
| Lansoprazole | 8.7 |
| Pantoprazole | 33.1 |
| Rabeprazole | 39.8 |

Test Example 4
(Human CYP1A Induction Test)

CYP1A specifically participates in a metabolism reaction from 7-ethoxyresorufin to resorufin. Therefore, by use of HepG2 cells, the production amount of resorufin in exposure to test substance, served as an index for CYP1A activity, was determined, whereby CYP1A inducing action was investigated.

(a) Exposure to HepG2 Cells and Preparation of Samples

HepG2 cells (purchased from Dainippon Pharmaceutical Co., Ltd.) were cultured in a medium containing inactivated calf serum (450 mL minimum essential medium supplemented with 5 mL sodium pyruvate (100 mM), 5 mL nonessential amino acid (×100), 5 mL antibiotic, antifungal solution (10,000 units penicillin, 10 mg streptomycin, 25 μg amphotericin B/mL), 5 mL L-glutamine solution (200 mM), and 50 mL inactivated calf serum). Following the incubation performed for about 7 days (70–80% confluence), the medium was removed by aspiration. A fresh medium (10 mL), and a 5 μL solution of the test substance in dimethyl sulfoxide (DMSO) were added, followed by incubation for 24 hours at 37° C. The medium employed for incubation has a DMSO concentration of 0.05%, a test substance concentration of 20 μM, a β-naphthoflavone (positive control) concentration of 20 μM, and 3-methylcholanthrene (positive control) concentration of 0.1 μM. When 24 hours had elapsed, the medium was removed by aspiration, followed by washing twice with 5 mL phosphate buffer (37° C.). Subsequently, a mixture of an ice-cold phosphate buffer (0.5M, pH 7.4) and EDTA (0.5 mM) (20:10) was diluted 3-fold, and the diluted solution was added (4 to 5 mL) to the cells. The cells were scraped off by use of a cell scraper, and then homogenized with glass homogenizer under cooling on ice, to thereby prepare a sample to be used in the following test.

(b) Metabolizing Activity Test

A 10 μL solution of 78 μM 7-ethoxyresorufin in DMSO was added to the cell homogenate (890 μL). 100 μL NADPH-Generating system (a mixture of 60 mM $MgCl_2$, 6.7 mg/mL β-$NADP^+$, 27.2 mg/mL G-6-P, and 10 μL/mL G-6-Pdh) was added, and reaction was immediately initiated at 37° C.

Incubation was performed for 10 or 20 minutes at 37° C. Subsequently, aqueous 17% potassium carbonate solution (100 μL) was added, to thereby stop the reaction.

(c) Quantitation Method

After the reaction was stopped, the reaction mixture was subjected to centrifugation at 3,000 rpm for 20 minutes. The resorufin content of the supernatant was measured by use of a fluorometer (excitation: 550 nm, fluorescence: 586 nm). The general procedure described above was repeated by use of a resorufin solution, whereby a calibration curve was created.

The protein concentration of a test sample was measured as follows. A 2.5 mL protein assay solution (Bio-Rad) diluted 5-fold was added to the cell homogenate (100 μL). The mixture was allowed to stand for 30 minutes at room temperature, followed by measurement of the protein concentration by use of a fluorometer (wavelength: 595 nm). A calibration curve for determining protein concentration was generated by use of human albumin (product of Sigma).

When a resorufin concentration was obtained, the concentration was divided by the metabolism reaction time and the protein concentration of the sample, whereby a metabolizing rate was calculated. Resorufin production rate under exposure to a positive control substance, omeprazole, was taken as 100%, and a corresponding rate under exposure to a test substance was computed, which was employed as an index for CYP1A inducing activity. The results are shown in Table 4.

TABLE 4

| Test compound | CYP1A2-inducing ability (%) |
|---|---|
| Example 1(2) | 7.6 |
| Example 2(2) | 7.14 |
| Example 3(2) | 10.6 |
| Example 4 | 6.2 |
| Example 5(1) | 10.8 |
| Example 6(1) | 7.9 |
| Example 9(3) | 4.4 |
| Example 10(2) | 7.7 |
| Example 11 | 4.9 |
| Example 12 | 11.6 |
| Omeprazole | 100 |
| Esomeprazole | 91.3 |
| Lansoprazole | 47.1 |
| Pantoprazole | 14.5 |
| Rabeprazole | 344.2 |

As is apparent from Tables 1 to 4, the compounds of the present invention exhibit excellent proton pump inhibitory action and gastric acid secretion inhibitory action. Moreover, the high levels, as high as 60% or more, of the index of CYP2C19 activity indicate that the compounds of the present invention were less metabolized by CYP2C19, revealing less difference between subjects in terms of therapeutic effect. Also, the low levels, as low as about 10% or less, of the index of CYP1A2 inducing activity indicate high safety of the compounds of the present invention. In contrast, the index values of CYP2C19 activity as measured for the conventional proton pump inhibitors are very low (less than 40%), which indicate that they were considerably metabolized by CYP2C19, leading to different therapeutic responses between subjects. In addition, most of the conventional proton pump inhibitors exhibited considerably high CYP1A2 inducing activity.

INDUSTRIAL APPLICABILITY

The compounds of the present invention exhibit therapeutic effect with less difference between subjects, although the individuals exhibit different CYP2C19 activity, patients can equally enjoy the same proper therapeutic effect with the same amount of administration. Moreover, since the compounds of the present invention have low risk of drug interaction attributable to induction of CYP1A family enzymes and low risk of canceration, the compounds are useful as peptic ulcer remedies which provide therapeutic effect safely and reliably.

What is claimed is:
1. A Benzimidazole derivative represented by the following formula (1):

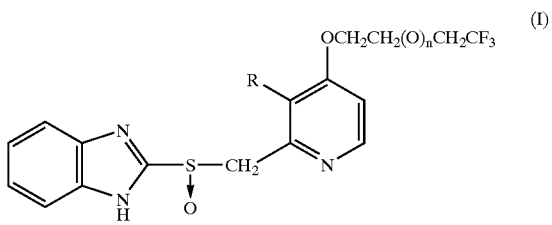

(wherein R represents a hydrogen atom or a methoxy group, and n is 0 or 1) or a salt thereof.

2. The benzimidazole derivative or a salt thereof according to claim 1, which is a compound selected from the group consisting of 2-[3-methoxy-4-(4,4,4-trifluorobutoxy) pyridin-2-yl-methanesulfinyl]-1H-benzimidazole, 2-{3-methoxy-4-[2-(2,2,2-trifluoroethoxy)ethoxy]pyridin-2-yl-methanesulfinyl}-1H-benzimidazole, (+)-2-[3-methoxy-4-(4,4,4-trifluorobutoxy)pyridin-2-yl-methanesulfinyl]-1H-benzimidazole, (+)-2-3-methoxy-4-[2-(2,2,2-trifluoroethoxy)ethoxy]pyridin-2-yl-methanesulfinyl}-1H-benzimidazole, (−)-2-[3-methoxy-4-(4,4,4-trifluorobutoxy) pyridin-2-yl-methanesulfinyl]-1H-benzimidazole, (−)-2-{3-methoxy-4-[2-(2,2,2-trifluoroethox)ethoxy]pyridin-2-yl-methanesulfinyl)-1H-benzimidazole, and a salt thereof.

3. The benzimidazole derivative or a salt thereof according to claim 1, which is a compound selected from the group consisting of 2-[4-(4,4,4-trifluorobutoxy)pyridin-2-yl-methanesulfinyl]-1H-benzimidazole, 2-{4-[2-(2,2,2-trifluoroethoxy)ethoxy]pyridin-2-yl-methanesulfinyl}-1H-benzimidazole, (+)-2-[4-(4,4,4-trifluorobutoxy)pyridin-2-yl-methanesulfinyl]-1H-benzimidazole, (+)-2-{4-[2-(2,2,2-trifluoroethoxy)ethoxy]pyridin-2-yl-methanesulfinyl}-1H-benzimidazole, (−)-2-[4-(4,4,4-trifluorobutoxy)pyridin-2-yl-methanesulfinyl}-1H-benzimidazole, (−)-2-(4-[2-(2,2,2-trifluoroethoxy)ethoxy]pyridin-2-yl-methanesulfinyl}-1H-benzimidazole, and a salt thereof.

4. A medicinal composition comprising a benzimidazole derivative or a salt thereof as recited in any one of claims 1 to 3 and a pharmacologically acceptable carrier.

5. A method for suppressing secretion of gastric acid characterized by administering an effective amount of the benzimidazole derivative or a salt thereof as recited in any one of claims 1 to 3.

6. A method for treating a peptic ulcer characterized by administering an effective amount of the benzimidazole derivative or a salt thereof as recited in any one of claims 1 to 3.

7. The benzimidazole derivative or a salt thereof according to claim 1, wherein R represents a hydrogen atom.

8. The benzimidazole derivative or a salt thereof according to claim 1, wherein R represents a methoxy group.

9. The benzimidazole derivative or a salt thereof according to claim 1, wherein n is 0.

10. The benzimidazole derivative or a salt thereof according to claim 1, wherein n is 1.

11. The benzimidazole derivative or a salt thereof according to claim 1, which is said salt thereof.

* * * * *